(12) United States Patent
Moussa et al.

(10) Patent No.: US 7,695,918 B2
(45) Date of Patent: *Apr. 13, 2010

(54) PROCESS FOR DETECTING $PrP^{SC}$ USING AN ANTIBIOTIC FROM THE FAMILY OF AMINOGLYCOSIDES

(75) Inventors: Aly Moussa, Oullins (FR); Anthony William Coleman, Calluire-et-Cuire (FR); Anna Bencsik-Reynier, Charly (FR); Patrick Shahgaldian, Lyons (FR); Hervé Perron, Saint-Genis-les-Ollières (FR); Ambroise Martin, Charly (FR)

(73) Assignees: Agence Francaise de Securite Sanitaire des Aliments-AFSSA (FR); Centre National de la Recherche Scientifique-CNRS (FR); Universite Claude Bernard Lyon (FR); Biomerieux (FR)

( * ) Notice: Subject to any disclaimer, the term of this patent is extended or adjusted under 35 U.S.C. 154(b) by 234 days.

This patent is subject to a terminal disclaimer.

(21) Appl. No.: 11/151,066

(22) Filed: Jun. 13, 2005

(65) Prior Publication Data

US 2006/0014215 A1    Jan. 19, 2006

Related U.S. Application Data (63) Continuation of application No. PCT/FR03/03856, filed on Dec. 19, 2003.

(30) Foreign Application Priority Data

Dec. 20, 2002    (FR) .................................. 02 16382

(51) Int. Cl.
*G01N 33/48* (2006.01)
*C07H 15/22* (2006.01)
*A01N 43/04* (2006.01)

(52) U.S. Cl. .......................... 435/7.1; 436/14; 514/37

(58) Field of Classification Search ................ None
See application file for complete search history.

(56) References Cited

U.S. PATENT DOCUMENTS 3,993,544 A * 11/1976 Demain et al. ............... 435/81

6,221,614 B1    4/2001 Prusiner et al.
6,322,802 B1 * 11/2001 Prusiner et al. ............. 424/405
6,765,088 B1 * 7/2004 Korth et al. ............. 530/388.1
2008/0176256 A1 * 7/2008 Benscik-Reynier et al. 435/7.92

FOREIGN PATENT DOCUMENTS

| WO | 98/50576 | 11/1998 |
| WO | WO 01/23425 A1 | 4/2001 |
| WO | 01/56380 A1 | 8/2001 |
| WO | WO 02/33420 A2 | 4/2002 |
| WO | WO 02/086511 A2 | 10/2002 |

OTHER PUBLICATIONS

Moussa et al (2006) Chem. Commun. 973-975.*
Luna and Roberts (1998) Journal of Antimicrobial Chemotherapy. 42: 613-619.*
Fabrizio Tagliavini et al., "Tetracycline Affects Abnormal Properties of Synthetic PrP Peptides and $PrP^{Sc}$ in vitro", Journal of Molecular Biology, vol. 300, No. 5, Jul. 28, 2000, pp. 1309-1322.
U. K. Laemmli, "Cleavage of Structural Proteins during the Assembly of the Head of Bacteriophage T4," Nature vol. 227 (1970); vol. 227, pp. 680-685.
Vicki A. Luna and Marilyn C. Roberts, "The Presence of the *tetO* Gene in a Variety of Tetracycline-Resistant *Streptococcus pneumoniae* Serotypes from Washington State," Journal of Antimicrobial Chemotherapy (1998), 42, pp. 613-619.
J.-Y. Madec, et al., "Protease-Resistant Prion Protein in Brain and Lymphoid Organs of Sheep within a Naturally Scrapie-Infected Flock," Microbial Pathogenesis 2000, 28, pp. 353-362.
Aly Moussa, et al., "Use of Streptomycin for Precipitation and Detection of Proteinase K Resistant Prion Protein ($PrP^{SC}$) in Biological Samples." Chem. Commum. 2006, pp. 973-975.
The Merck Index, 12$^{th}$ edition, 1996, p. 1507, product 8983.
D. Yala et al., "Class and Action Mechanism of Antibiotics," Medecine du Maghreb 2001, No. 91.

* cited by examiner

*Primary Examiner*—Zachariah Lucas
*Assistant Examiner*—Michelle Horning
(74) *Attorney, Agent, or Firm*—DLA Piper LLP (US)

(57) ABSTRACT

A process of concentration by precipitation of $PrP^{sc}$ for detecting or diagnosing $PrP^{sc}$, wherein a tissue or biological fluid stemming from or obtained from an animal or human organism is brought together with an antibiotic from the family of aminoglycosides, preferably streptomycin or one of its derivatives. The use of such an antibiotic for eliminating $PrP^{sc}$ from a tissue or biological fluid and a kit for diagnosing pathologies associated with the presence of $PrP^{sc}$ is also disclosed.

12 Claims, 7 Drawing Sheets

FIG.4A High
1 2 3 4 5 6 7

FIG.4B Middle
1 2 3 4 5 6 7 8

FIG.4C Low
1 2 3 4 5 6 7 8

| Animal | Results | Strep | Standard Method | Confirmation with ELISA or IHC | Totally confirmed |
|---|---|---|---|---|---|
| Bovine | Positive | 42 | 40 | 2 IHC* | 42 positive |
| Bovine | Negative | 14 | 14 | 0 | 14 negative |
| Bovine | | | | | 56 |
| Ovine | Positive | 38 | 32 | 6 ELISA | 38 positive |
| Ovine | Negative | 3 | 3 | 0 | 3 negative |
| Ovine | | | | | 41 |

IHC*: immunohistochemistry technology

| Tracks | Deposits |
|---|---|
| 1 | PM |
| 2 | LCR (−) + S (50 mg/mL) |
| 4 | LCR (−) + S (100 mg/mL) |
| 6 | LCR (−) + S (200 mg/mL) |
| 7 | LCR (+) + S (50 mg/mL) |
| 9 | LCR (+) + S (100 mg/mL) |
| 11 | LCR (+) + S (200 mg/mL) |
| 12 | PositiveBrainControl |

| Tracks | Deposits | Strepto |
|---|---|---|
| 1 | PM | |
| 2 | LCR ND | Without |
| 3 | 0.5 μg/mgLCR D/pK | |
| 4 | 1 μg/mgLCR D/pK | |
| 5 | LCR ND | With |
| 6 | 0.5 μg/mgLCR D/pK | |
| 7 | 1 μg/mgLCR D/pK | |
| 8 | Bottom WG ND | |
| 9 | BottomWD D/pK p.5 μg/mg | |

PROCESS FOR DETECTING PRP$^{SC}$ USING AN ANTIBIOTIC FROM THE FAMILY OF AMINOGLYCOSIDES

RELATED APPLICATION

This is a continuation of International Application No. PCT/FR2003/003856, with an international filing date of Dec. 19, 2003 (WO 2004/059321 A1, published Jul. 15, 2004), which is based on French Patent Application No. 02/16382, filed Dec. 20, 2002.

FIELD OF THE INVENTION

This invention relates to a method of total precipitation of PrP$^{sc}$ by streptomycin sulfate and its use for the immunodetection or elimination of PrP$^{sc}$ from liquids or solutions.

BACKGROUND

The native or normal prion protein, designated "PrP" or "PrP$^c$", for the cellular prion protein is a glycoprotein broadly expressed in the lymphoid and neuronal cells of mammals.

Conformational changes of PrP$^c$ result in the appearance and propagation of the protein pathogen PrP$^c$ that is resistant to the proteinase K. This protein pathogen can be indifferently called "PrP$^{sc}$" or "PrP$^{res}$." Accumulation of PrP$^{sc}$ in the organs of animals is at the origin of numerous diseases and especially of trembling in small ruminants, of the chronic cachetic disease (or chronic wasting disease "CWD") of the elk and antelope, bovine spongiform encephalopathy (ESB) and Creutzfeld-Jakob disease (MCJ) in humans.

The delayed appearance after an incubation period of 2 to 6 years and slow development of symptoms in cattle infected with ESB has considerably slowed the development of epidemiological models. ESB is transmissible by ingestion to humans and has resulted in the appearance of a new form of Creutzfeld-Jakob disease (vMJC).

Detection of the protein pathogen PrP$^{sc}$ is difficult in infected animals healthy before the development of the disease and especially in the blood and urine of diseased animals. It has been established that PrP$^{sc}$ present in animals intended for human consumption is transmitted to man by ingesting infected tissues. Thus, a major objective of public health is to avoid this transmission by detecting the presence of PrP$^{sc}$ in animals intended for human consumption to remove them from the food chain.

Detecting the presence of PrP$^{sc}$ in biological samples or in animals has thus become extremely important and several research teams are developing methods of immunological detections (WO 02/086551). Moreover, methods of complexing peptides, small molecules or inhibitors to PrP$^{sc}$ to treat vMJC constitute the subject of active research. However, prior methods have constantly come up against the difficulty of identifying PrP$^{sc}$ in a reliable manner when it is in a low quantity in a biological sample.

SUMMARY OF THE INVENTION

This invention relates to a process for detecting PrP$^{sc}$ including contacting a tissue or biological fluid stemming from or obtained from an animal with an antibiotic from the family of aminoglycosides.

This invention also relates to a method of eliminating PrP$^{sc}$ from tissue or a biological fluid including contacting a suspension of the tissue or biological fluid with an aminoglycoside to precipitate the PrP$^{sc}$, and separating precipitated PrP$^{sc}$ from the suspension.

This invention further relates to a kit for diagnosing pathologies associated with the presence of PrP$^{sc}$ including an aminoglycoside.

BRIEF DESCRIPTION OF THE DRAWINGS

FIG. 8 a shows the results of a Western blot of samples of LCR(+) and of LCR(−) in MJC digested or not digested by proteinase K in accordance with a range of concentration and treated or not treated with streptomycin. The immunological disclosure is assured by an anti-prion antibody. Table 8B summarizes the deposits made in the tracks of FIG. 8A.

DETAILED DESCRIPTION

We have demonstrated a new property of aminoglycosides and, in particular, aminoglycosides of Group II and, more particularly, streptomycin. We have also demonstrated the capacity of the antibiotics to form a complex with PrP$^{sc}$ and make it precipitate.

Figure 1A:
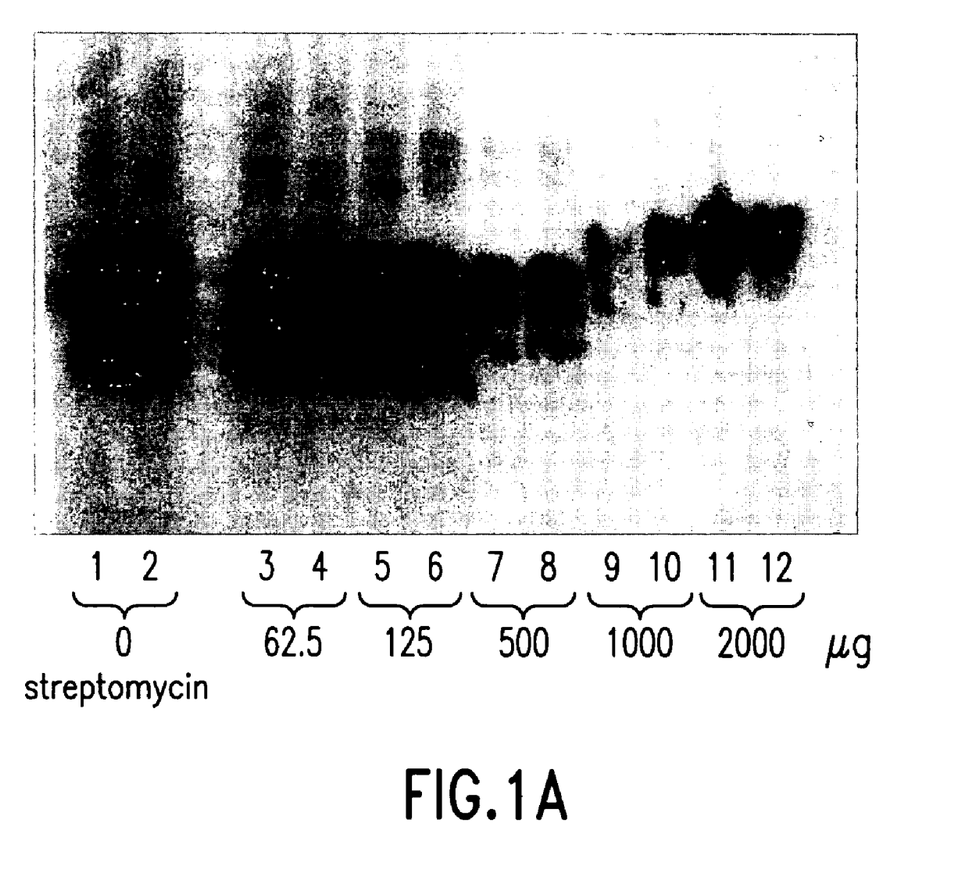
FIG. 1A is a comparative example of the detection after gel electrophoresis of 15% polyacrylamide, transfer and immunodetection of PrP$^{sc}$ in a brain sample of a sheep affected with trembling and placed in the presence of more or less significant quantities of streptomycin.
Figure 1B:
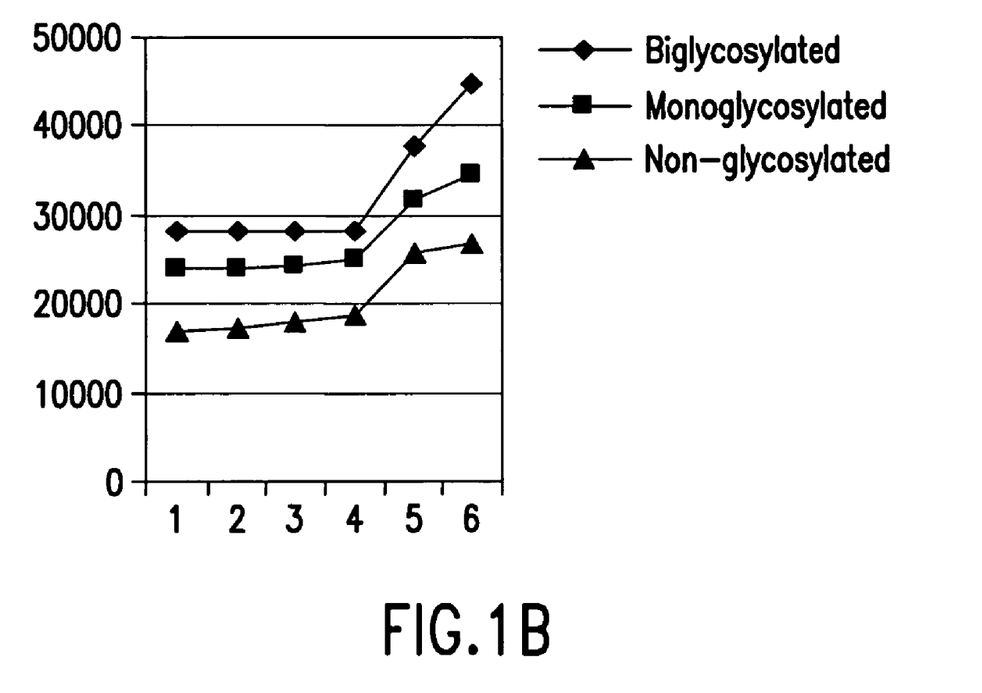
FIG. 1B is a graphic comparing the average molecular weight measured for each PrP$^{sc}$ band of FIG. 1 before and after being mixed with increasing quantities of streptomycin.

We thus discovered that addition of an aminoglycoside in a biological sample stemming from various animal origins and containing prions has the consequence of causing the apparent molecular mass to increase by 3 bands of prions. This discovery and the experiments that followed allowed us to demonstrate that aminoglycoside forms a complex with $PrP^{sc}$ and this complexing precipitates $PrP^{sc}$ and significantly increases the possibilities of detecting $PrP^{sc}$ over the methods previously used.

The invention thus relates to a process for concentrating $PrP^{sc}$ by precipitation for use in diagnosing diseases due to prions or eliminating prions present in a biological liquid and characterized in that a suspension of tissue or biological fluid stemming from or obtained from an animal or human organism is brought together with an antibiotic preferably selected from the family of aminoglycosides and preferably streptomycin.

More precisely, the process in accordance with aspects of the invention comprises the following steps:

a) an aminoglycoside is added to a suspension of a tissue or a biological fluid stemming or obtained from an animal or human organism, b) the solution is placed in a suitable buffer and subjected to heating and the solution obtained is then centrifuged and the bottom portion is separated from the supernatant, and c) the $PrP^{sc}$ is detected after migration onto an electrophoretic gel, transfer and immunodetection.

The process of the invention can also comprise a supplementary step of digesting the sample to be dosed by a proteinase and especially proteinase K. Thus, the process of the invention comprises the following steps:

a) a proteinase, e.g., proteinase K, is added to a suspension of a tissue or of a biological fluid stemming or obtained from an animal or human organism, b) an aminoglycoside is added, c) the solution is placed in a suitable buffer and subjected to heating and the solution obtained is then centrifuged and the bottom portion is separated from the supernatant, and d) the $PrP^{sc}$ is detected after migration onto an electrophoretic gel, transfer and immunodetection.

More precisely, the process of the invention comprises the following steps:

a) the preparation of about a 10% suspension by homogenization of biological fluid or tissue obtained from an animal or human organism in about a 5% glucose solution, b) proteinase K is added to about 100 μl of the suspension obtained, that is then incubated at about 37° C. for about one hour, c) an aminoglycoside is added to the suspension, that is then incubated for about a second hour at about 37° C., d) the solution is placed in a suitable buffer and subjected to heating and the solution obtained is then centrifuged and the bottom portion is separated from the supernatant, e) the bottom is suspended in about 50 μl of a solution of 50% v/v 8M urea and of the Laemmli denaturing buffer as described by Laemmli, Nature 227 (1970), pp. 680-685, f) after a vigorous vortex agitation, the mixture is heated for about 5 min at about 100° C., centrifuged to 12,000 g and the supernatants recovered to cause them to migrate onto SDS PAGE, g) after migration onto an electrophoretic gel, especially one-dimensional electrophoresis on 15% polyacrylamide dodecylsulfate gel (SDS PAGE) as described by Laemmli, Nature 227 (1970), pp. 680-685, the proteins are transferred by electrophoresis onto nitrocellulose membranes and immunoblotted at ambient temperature for about 60 minutes with a monoclonal antibody recognizing a specific epitope constituted of amino acids 126-160, wherein the secondary antibody (1/5000) is a goat antibody directed against heavy and light chains of mouse immunoglobulins conjugated to horseradish peroxidase (IgG H+L), and h) the blots are then washed and signals detected by chemiluminescence either with an ECL kit (Amersham) on films (Biomex light, Kodak) or with a super Signal Ultra (Pierce) and visualization on Fluor S. Multimager (BioRad).

The process in accordance with the invention has the advantage of not requiring ultracentrifugation. The process in accordance with the invention also relates to complexing aminoglycoside with the proteins of the prion and precipitation of the proteins of the prion by aminoglycoside.

The biological tissue may stem from or may be obtained from the brain or some other animal or human tissue or from a biological fluid such as cerebrospinal fluid or serum.

The proteinase is a proteinase selected for its ability to digest the proteins present, including the normal forms of the protein of the prion, and for its inability to digest the pathological forms of this protein. This is advantageously proteinase K.

The tissue may be homogenized in a solution of glucose that is preferably a 5% solution of glucose prior to being placed in contact with the aminoglycoside.

The heating step corresponds, after having added 100 μl of Laemmli buffer to the suspension resulting from the placing of the biological sample in contact with proteinase K and aminoglycoside, to an increase of temperature between about 60 and about 150° C., preferably approximately about 100° C.

The aminoglycoside may preferably be an aminoglycoside of Group II and preferably streptomycin or one of its derivatives.

The invention also concerns the use of such an aminoglycoside for precipitating, detecting, even in immunohistochemistry detection and/or diagnosis, $PrP^{sc}$.

The invention also concerns the use of such an aminoglycoside for eliminating $PrP^{sc}$ from a biological fluid.

Finally, the invention also concerns a kit for diagnosis of pathologies associated with the presence of $PrP^{sc}$, characterized in that it comprises such an aminoglycoside.

Other advantages and characteristics of the invention will appear from a reading of the following examples concerning the amplification of the detection of $PrP^{sc}$ when the biological sample is placed in the presence of an aminoglycoside.

Reference is made in these examples to be attached drawings.

The biological samples on which Examples 2 and 3 below were carried out were obtained from homogenate of bovine brain placed in a glucose solution at 5%. Volumes of 100 μl of this suspension corresponding to 10 mg of cerebral tissue were used for the following experiments. Each sample was thus constituted of 100 μl in which proteinase K was added. After one hour at 37° C. streptomycin was added or not added. The solution was agitated under vortex and incubated at 37° C. for another hour. After the addition of 100 μl denaturing Laemmli buffer, the mixture was heated for five min at 100° C. and centrifuged at 12,000 g for 5 min, after which the supernatants were recovered to be migrated onto SDS-PAGE. The bottoms were also covered and 50 μl of a 50% v/v solution of 8M urea and the Laemmli buffer added to them. After vigorous agitation under vortex, the mixture was heated for 5 min at 100° C. centrifuged at 12,000 g for 5 min, after which the supernatants were recovered to be migrated onto SDS-PAGE.

Example 1

Example 1 relates to FIGS. 1A and 1B concerning trials in which increasing concentrations (0 μg, 62.5 μg, 125 μg, 500 μg, and 2000 μg) of streptomycin were added to constant quantities of PrP$^{sc}$ extracted from the equivalent of 920 µg of sheep brain afflicted with trembling. Then, the mixture was centrifuged. The supernatant was used for immunological detection by Western blot (FIG. 1A) and measurement of the average molecular mass of bands of PrP$^{sc}$ (FIG. 1B). The results show that the increase of the quantity of streptomycin, namely, an addition of 0, 62.5, 125, 500, 1000 and 2000 µg, permits the observation that at the lowest concentrations of streptomycin the band of the non-glycosylated protein is the first to show an increase of the apparent molecular mass. Then, the complexing concerning the band of monoglycosylated protein and, finally, the biglycosylated protein is complexed when the concentration of streptomycin is the greatest.

The number of streptomycin molecules bound to each of the PrP$^{sc}$ bands at a given concentration was evaluated by measuring the molecular weight of each band. We estimate that the increase of the apparent molecular weight of each of the PrP$^{sc}$ bands in the presence of 2000 µg of streptomycin corresponds to attaching 10 to 12 molecules of streptomycin per band of PrP$^{sc}$.

Example 2

Figure 2:
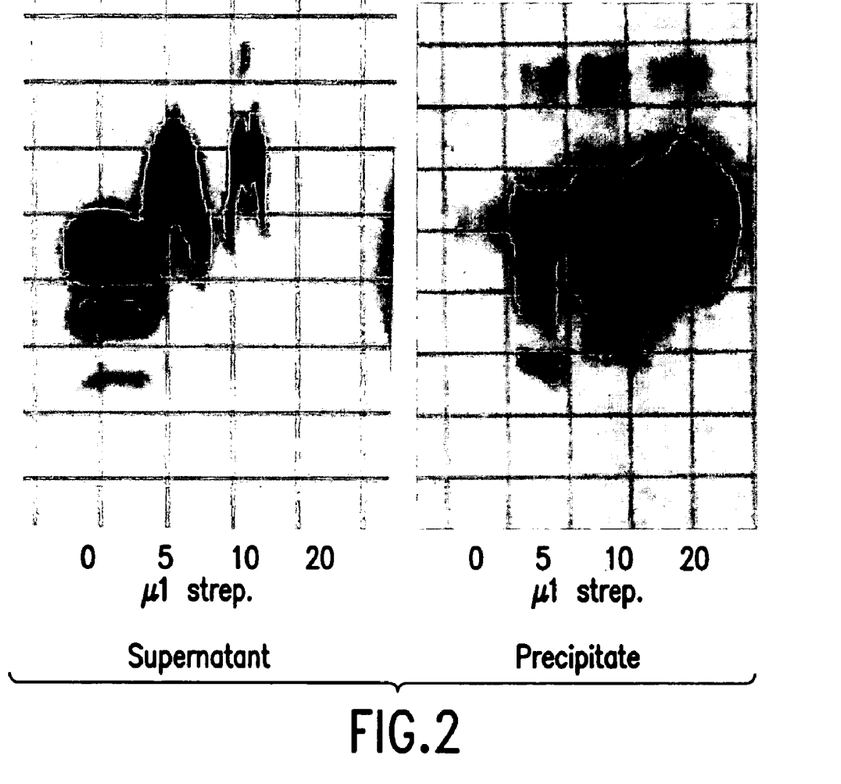
FIG. 2 is an example comparing the detection after gel electrophoresis of 15% polyacrylamide, transfer and immunodetection, of PrP$^{sc}$ in the supernatant and in the precipitates at the end of the second hour of incubation of a suspension very rich in protein PrP$^{sc}$ in the presence and the absence of a variable quantity of streptomycin.

Example 2 relates to FIG. 2 concerning trials in which increasing concentrations (0 µg, 5 µg, 10 µg, and 20 µg) of streptomycin at 1 g/ml were added to constant quantities of the biological sample prepared as indicated above. In the absence of streptomycin, all the PrP$^{sc}$ bands are identified as being in the supernatant. They are detected progressively and simultaneously in the bottom and in the supernatant. The quantity of PrP$^{sc}$ present in the supernatant diminished progressively while the quantity increased progressively in the precipitates. The addition of 20 µl of streptomycin totally precipitated the PrP$^{sc}$, that was then detected only in the precipitates.

Example 3

Figure 3:
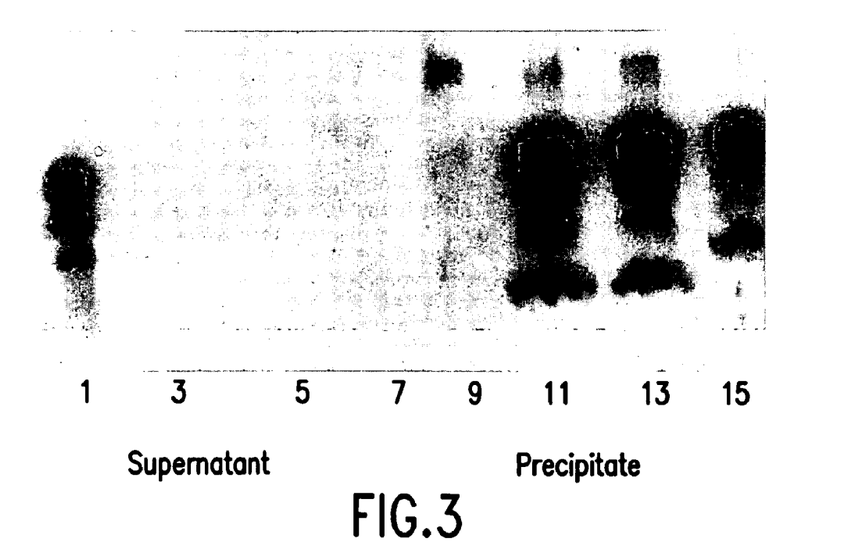
FIG. 3 shows that the simultaneous addition of proteinase K and streptomycin to a suspension containing a small quantity of PrP$^{sc}$ has as a consequence the disappearance of the PrP$^{sc}$ from the supernatant and its appearance in the precipitates.

Example 3 relates to FIG. 3.

The experiment of Example 2 was repeated, but with the same brain sample diluted to 1/25 relative to Example 2 and reducing the incubation period to one hour after the simultaneous addition of proteinase K and streptomycin to the brain suspensions. The result is that PrP$^{sc}$ bands were only detected in the supernatant in the absence of streptomycin and in the bottom in the presence of any concentration of streptomycin.

Example 4

Figure 4A:
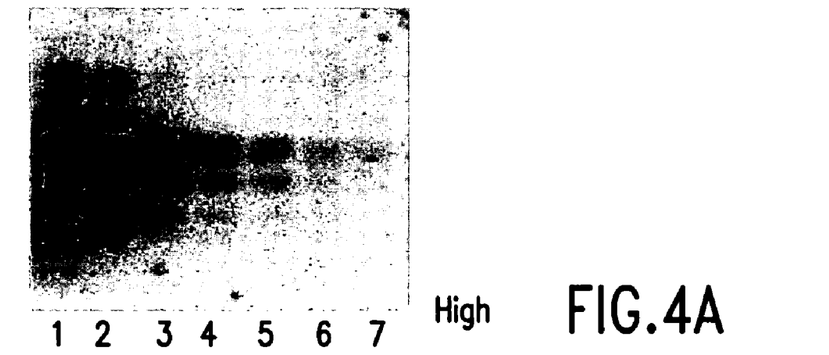
FIGS. 4A, 4B and 4C show, after gel electrophoresis of 15% polyacrylamide, transfer and immunodetection, the increase of the detection threshold of PrP$^{sc}$ during the addition of increasing quantities of streptomycin.
Figure 4B:
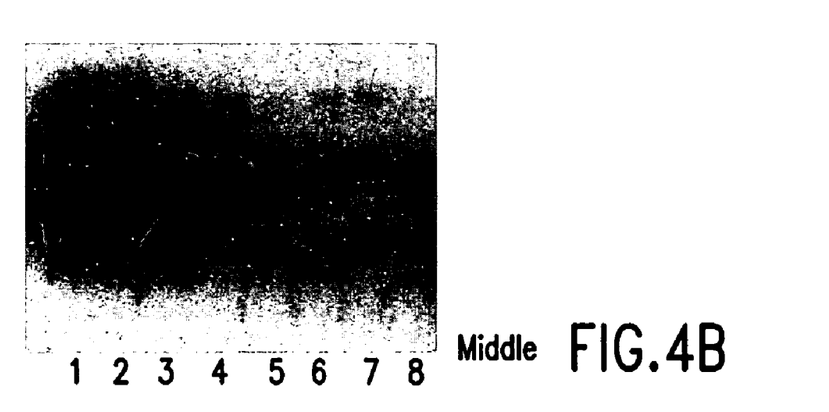
Figure 4C:
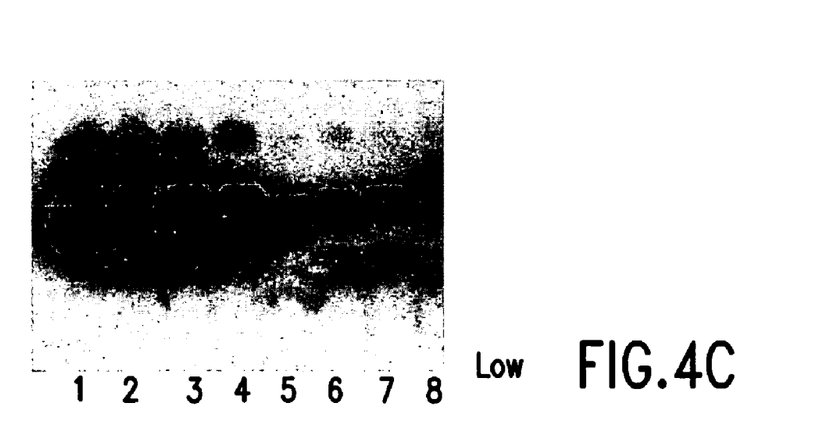
Figure 5:
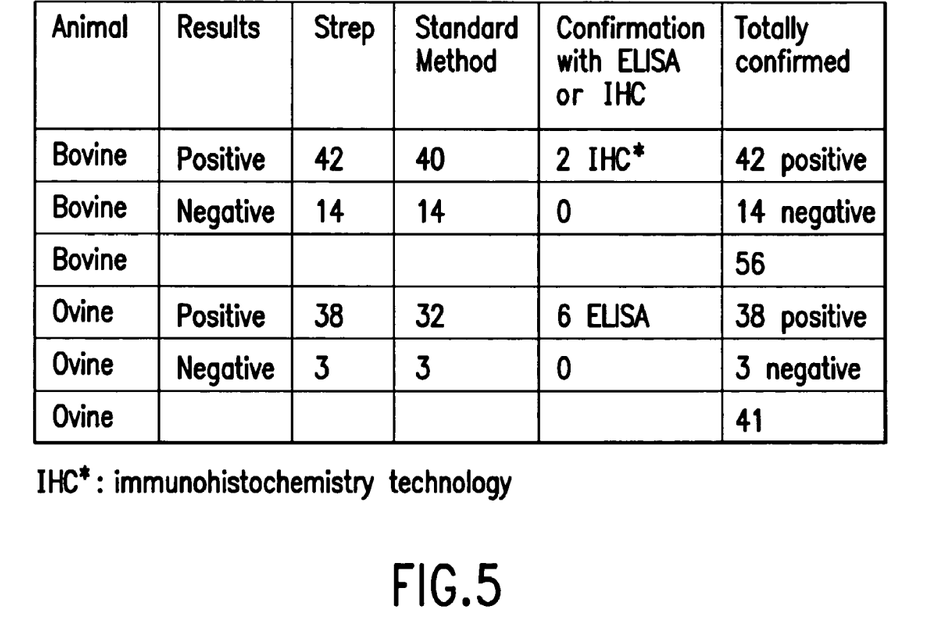
FIG. 5 is a table referring to Example 5 and showing a comparison of the results of the diagnosis of PrP$^{sc}$ in 97 animal brains obtained by the technique of the invention with those obtained by the reference technique.

Example 4 refers to FIGS. 4A, 4B and 4C.

Starting with a mother solution of 1:2 in a series of a homogenate with 10% bovine brain infected by ESB in a 5% glucose solution, 3 sets of tubes each containing 100 µl of the same dilution were prepared. 1 µg proteinase K in a volume of 10 µl was added to each tube of the first dilution set (from pure to 1/64). 5 µl streptomycin and 1 µl proteinase K in a volume of 10 µl were simultaneously added to each tube of the second set (from 1/2 to 1/256). 10 µl streptomycin and 1 µl proteinase K in a volume of 10 µl were simultaneously added to each tube of the third set (from 1/2 to 1/256).

All the tubes were incubated at 37° C. for one hour. Then, 100 µl of denaturing Laemmli buffer was added. The mixture was heated to 100° C. for five minutes, then centrifuged at 12,000 g for 5 minutes, and the supernatants recovered from the first set of tubes for depositing onto SDS-PAGE. The supernatants of the tubes of the second and third set of tubes were voided and 50 µl urea 8M at 50% v/v and of denaturing Laemmli buffer were added into each tube. After vigorous vortex agitation, the mixture was heated for 5 min at 100° C. centrifuged at 12,000 g and the supernatants for the second and third set of tubes were recovered.

FIG. 4A shows that the detection limit of PrP$^{sc}$ detected in the absence of streptomycin is at 1/16.

FIG. 4B shows the quantity of PrP$^{sc}$ precipitated in the presence of 5 µl streptomycin: the PrP$^{sc}$ is detectable down to a dilution of 1/128, which shows a broadly increased detection threshold.

FIG. 4C shows the quantity of PrP$^{sc}$ precipitated in the presence of 10 µl streptomycin: FIG. 4c shows that detection is possible and representative even on the most diluted samples (1/256).

Example 5

Comparative Example

The reference technique is based on the extraction of PrP$^{sc}$ from 1.2 ml cerebral homogenate (Madec et al., Microbia Pathogenesis, 28 (2000), pp. 353-362). The homogenates were forced through a needle with a diameter of 0.4 mm before being processed for one hour at 37° C. by 10 µg proteinase K per 100 mg cerebral tissue. After the addition of sarkosyl (10%) and 10 mM tris buffer (pH 7.4), the samples were incubated for 15 minutes at ambient temperature, then centrifuged at 245,000 g for 4 hours and 20° C. on a 10% saccharose cushion (Beckman TL 100 ultracentrifuge). Finally, the bottom portion was placed back in suspension in 50 µl denaturing Laemmli buffer for 5 minutes at 100° C. and centrifuged again for 5 min at 12,000 g. The supernatants were recovered for migration onto SDS PAGE.

According to a technique of the invention, 100 µl cerebral suspension obtained after grinding the brain described in the reference technique was used. 1 µg proteinase K was added and the mixture incubated for a first time for one hour. Then, 20 µl streptomycin was added and the mixture incubated a second time for one hour. Then, 100 µl denaturing Laemmli buffer was added. After 5 min of heating at 100° C. the mixture was centrifuged 2 min at 12,000 g. The supernatants were eliminated and then 50 µl 50% v/v urea 8M and denaturing Laemmli buffer were added. After vigorous vortex agitation, the mixture was heated for 5 min at 100° C. and centrifuged 2 min longer at 12,000 g. The supernatants were recovered for migration onto SDS PAGE.

The results are presented in Table 1. In conclusion, the use of streptomycin sulfate permits better detection of cases that are slightly positive and, in addition, allows a long and expensive ultracentrifugation to be avoided.

Example 6

Samples of recPrP (recombinant protein prion) were prepared by diluting a solution of recPrP (42 µM) with an equivalent volume of water or with a solution of streptomycin (1 g/ml). The reference for streptomycin alone was prepared using a solution of 0.5 g/ml.

The samples were prepared by depositing 10 µl of these solutions on freshly split mica and drying for 24 hours at 37° C.

An analysis was made by imagery with an AFM Explorer Thermomicroscope equipped with a tripod 100 µm scanner in non-contact mode using elevated resonance frequencies ($F_0$=320 kHz) of pyramidal cantilever with silicone probes at a scanning frequency of 1 Hz. Processing of the images was performed with SPMlab 5.1 software and presented non-filtered.

Figure 6:
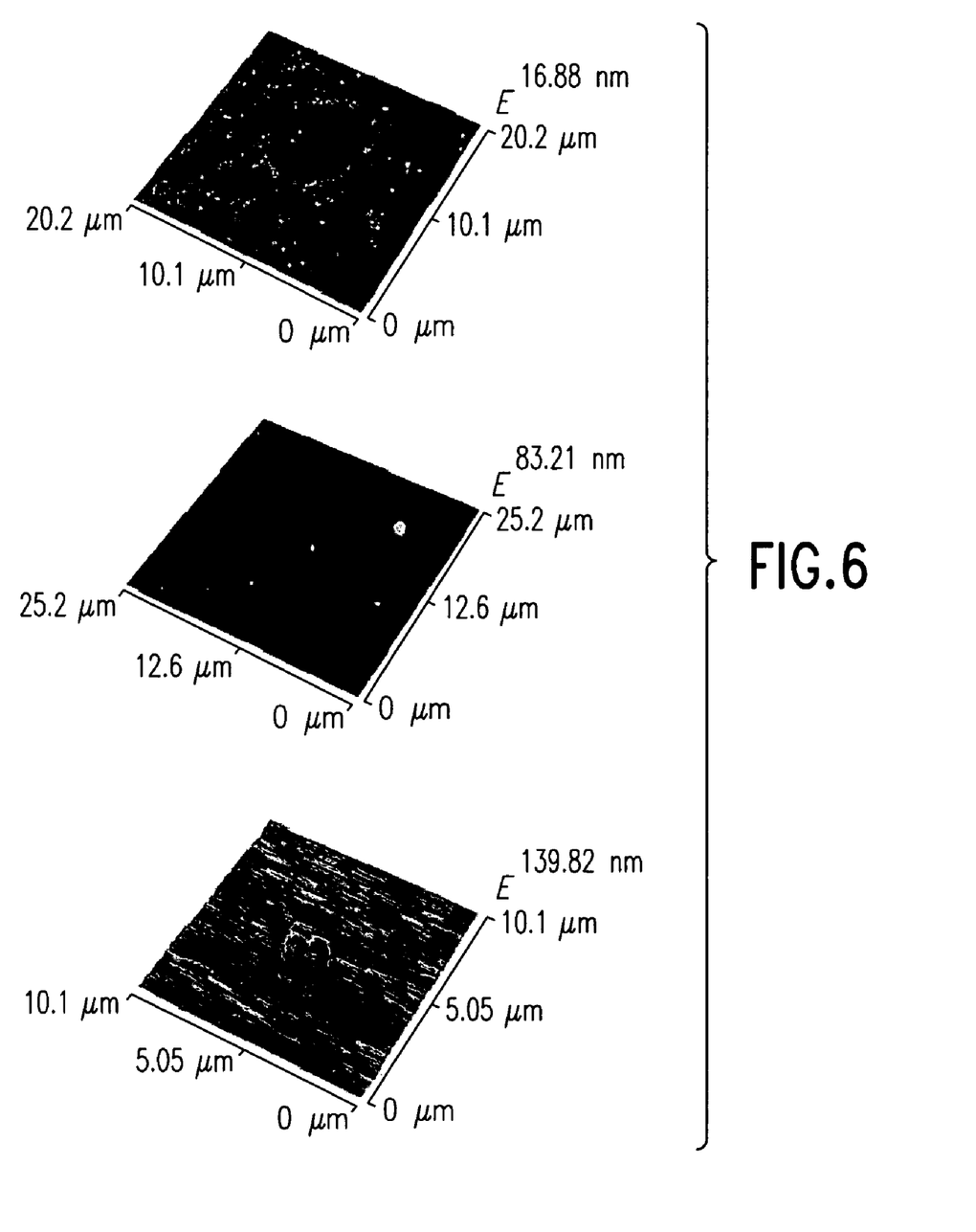
FIG. 6 shows images in scanning probe microscopy (SPM) in non-contact mode for dried films of recombinant protein prion (recPrP) alone (A), recPrP in the presence of streptomycin (B) and streptomycin alone (C).

It follows from FIG. 6 that the images of recPrP alone show a structure in characteristic circular aggregates. The films of streptomycin alone show an organization of pseudo-crystalline surface. The films containing the mixture show an amorphous surface: No crystalline or globular organization is observed. The interaction between streptomycin and PrP$^{sc}$ therefore inhibits the organizational surface properties of the two components of the mixture.

Example 7

Post mortem samplings of cerebrospinal fluid (LCR) that is preferably non-hemolyzed and without cellular debris were taken from patients not afflicted with MJC and patients afflicted with MJC. A sample of LCR from a patient not afflicted with MCJ and a sample of LCR from a patient afflicted with MCJ were placed in contact with a solution of streptomycin in a concentration range between 0.05 g/ml and 0.2 g/ml (0.05-0.1 and 0.2 g/ml). After vortex homogenization, the samples were incubated for 1 hour at 37° C. and then centrifuged for 5 minutes at 12,000 g.

The bottom portions obtained were put back by buffer of protein extraction. After being heated at 100° C. for 10 minutes, the samples were re-centrifuged for 5 min at 12,000 g. 15 µl of each supernatant was deposited on 12% bis-tris acrylamide gel SDS-PAGE. 5 µl of an extract of cerebral PrP$^{sc}$ colluded at 1/100 in the denaturation buffer was deposited in parallel under positive control. This extract was prepared in accordance with the reference protocol used for the diagnosis of Creutzfeld-Jakob disease. The electrophoretic migration was carried out under constant voltage (200 V) for 40 minutes in migration buffer concentrated once. The proteins were then transferred onto a membrane of PVDF activated by a semi-dry system between two graphite electrodes for 1 hour at a constant power (1 W). The direct immunological disclosure was then assured by the anti-prion antibody AC23 (that recognizes the region defined by the amino acids 145-154 of human PrP and the homologous regions of animal PrPs) at 0.5 µg/ml coupled with horseradish peroxidase.

Figure 7A:
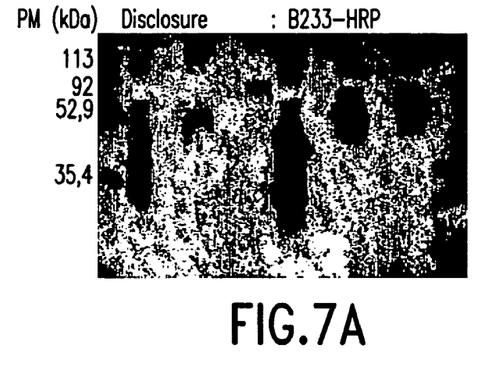
FIG. 7A is a comparative example of detection after gel electrophoresis 12% bis-tris acrylamide, transfer and immunodetection of the protein prion in samples of cerebrospinal fluid (LCR) of patients suffering from the Creutzfeld-Jakob disease (MCJ+) and patients not suffering from Creutzfeld-Jakob disease (MCJ−) treated with a range of streptomycin. Table 7B summarizes the deposits made in the tracks of FIG. 7A.
Figure 7B:
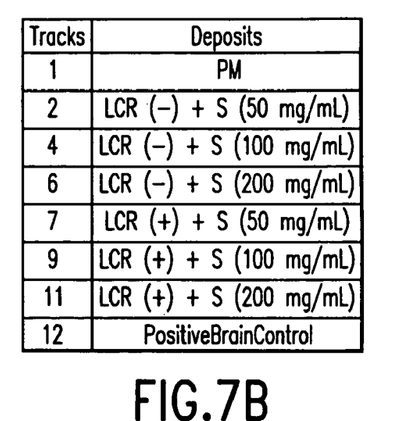

FIG. 7A shows that streptomycin bonds well to the protein prion in the absence of digestion by proteinase K. In fact, after treatment by streptomycin at 0.1 g/ml and 0.2 g/ml a single band is observed and its apparent molecular weight shifts in a manner proportional to the concentration of streptomycin. The apparent size of this band is approximately 50 kDa for 0.1 g/ml streptomycin. Moreover, the profile of the band (curved aspect, decay) suggests a molecular aggregation.

Example 8

An LCR from a patient not afflicted with MCJ and an LCR from a patient afflicted with MCJ were digested by proteinase K used at 0.5 µg/ml or 1 µg/ml. In parallel thereto, an aliquot of each sample did not undergo digestion by proteinase K. The digestion was carried out at 37° C. for 1 hour under gentle agitation. After digestion, the samples were incubated for 1 hour at 37° C. in the presence of 50 µg/ml final concentration streptomycin and a centrifugation for 5 minutes at 12000 g then followed.

The proteins were then extracted and denatured by heating in the presence of protein denaturation buffer and then analyzed by Western blot in conformity with the protocol of Example 7. The direct immunological disclosure was performed with the aid of AC23 antibody (used with 0.5 µg/ml) coupled with horseradish peroxidase.

Figure 8A:
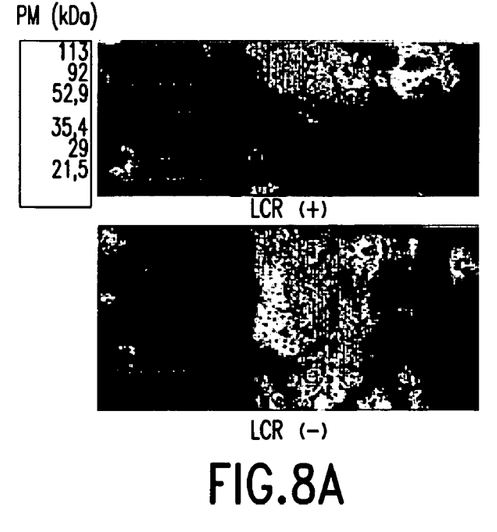
Figure 8B:
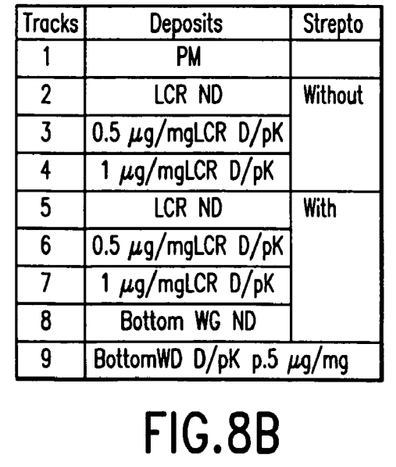

FIG. 8A shows that a single, low-intensity band was observed when the sample was treated with streptomycin. This band of approximately 35 kDa of apparent molecular mass was visible for the negative sample only in the absence of digestion by proteinase K (track 5 of the LCR (−) gel) whereas it was visible for the positive sample whatever the concentration of proteinase used was (tracks 5, 6 and 7 of the LCR (+) gel, characteristic of the resistant form of the protein prion.

Detection of the protein prion in the LCR was made possible by the use of streptomycin. In fact, in the absence of digestion by proteinase K, detection of the total PrP (cellular and pathological) is amplified in the presence of streptomycin and PrP$^{sc}$ is preferentially detected in an unexpected manner. After digestion by proteinase K, this technology permits the demonstration of a significantly different signal between the LCR from patients not afflicted with Creutzfeld-Jakob disease and the LCR from patients afflicted by this same disease. Therefore, streptomycin is important for detecting PrP$^{res}$ in biological fluids.

Furthermore, aminoglycosides such a streptomycin can be used for eliminating PrP$^{sc}$ by precipitating PrP$^{sc}$ after contact with the aminoglycosides.

The invention claimed is:

1. A process for detecting PrP$^{sc}$ comprising:
   a) contacting a tissue or biological fluid stemming from, or obtained from, an animal with an aminoglycoside antibiotic selected from group consisting of streptomycin and derivatives thereof; and
   b) immunodetecting an aminoglycoside antibiotic/PrP$^{sc}$ complex formed in step a).

2. The process according to claim 1, further comprising:
   a) adding the aminoglycoside antibiotic to a suspension of the tissue or the biological fluid to form a solution,
   b) placing the solution in a buffer and subjecting the solution to heating, centrifuging a resulting solution and separating a bottom portion from the supernatant, and
   c) detecting the aminoglycoside antibiotic/PrP$^{sc}$ complex in said bottom portion after migration onto an electrophoretic gel.

3. The process according to claim 1, wherein:
   a) adding a proteinase to a suspension of the tissue or the biological fluid,
   b) adding the aminoglycoside antibiotic to form a solution,
   c) placing the solution in a buffer, subjecting the solution to heating, centrifuging a resulting solution and separating a bottom portion from the supernatant, and
   d) detecting the aminoglycoside antibiotic/PrP$^{sc}$ complex in said bottom portion after migration onto an electrophoretic gel.

4. The process according to claim 1, wherein the biological tissue is from an animal or human brain or other tissue.

5. The process according to claim 3, wherein the proteinase is a proteinase K.

6. The process according to claim 1, wherein the tissue or biological fluid is homogenized in a solution of glucose prior to being placed in contact with the aminoglycoside antibiotic.

7. The process according to claim 1, wherein the heating corresponds to an increase in temperature between about 60 and about 150°.

8. The process according to claim 1, wherein the aminoglycoside antibiotic is streptomycin.

9. A method of eliminating PrP$^{sc}$ from tissue, or a biological fluid, comprising contacting a suspension of the tissue or biological fluid with an aminoglycoside antibiotic selected from the group consisting of streptomycin and derivatives thereof to precipitate the $PrP^{sc}$, and separating precipitated $PrP^{sc}$ from the suspension.

10. The method according to claim 9, wherein the aminoglycoside antibiotic is streptomycin.

11. A method for the precipitation of $PrP^{sc}$ during detection in a sample by immunohistochemistry comprising contacting $PrP^{sc}$ in a sample with an aminoglycoside antibiotic selected from the group consisting of streptomycin and derivatives thereof, whereby the $PrP^{sc}$ is precipitated.

12. A method according to claim 11 where the aminoglycoside antibiotic is streptomycin.

* * * * *